US00PP29704P3

(12) United States Plant Patent
Nakashima

(10) Patent No.: US PP29,704 P3
(45) Date of Patent: Sep. 25, 2018

(54) ROSE PLANT NAMED 'RNF PURPLE 01'

(50) Latin Name: ***Rosa* L.**
Varietal Denomination: RNF Purple 01

(71) Applicant: Kaneya Co., Ltd., Chita, Aichi (JP)

(72) Inventor: Hitoshi Nakashima, Gifu (JP)

(73) Assignee: Kaneya Co., Ltd., Aichi (JP)

( * ) Notice: Subject to any disclaimer, the term of this patent is extended or adjusted under 35 U.S.C. 154(b) by 205 days.

(21) Appl. No.: 14/999,308

(22) Filed: Apr. 21, 2016

(65) Prior Publication Data

US 2018/0035583 P1 Feb. 1, 2018

(51) Int. Cl.
*A01H 5/02* (2018.01)
*A01H 6/74* (2018.01)

(52) U.S. Cl.
USPC ..... Plt./148
CPC ..... *A01H 5/02* (2013.01); *A01H 5/0222* (2013.01); *A01H 6/749* (2018.05)

(58) Field of Classification Search
USPC ..... Plt./107, 114, 121, 128, 137, 148
CPC ..... A01H 5/0222
See application file for complete search history.

*Primary Examiner* — Kent L Bell
(74) *Attorney, Agent, or Firm* — The Webb Law Firm

(57) ABSTRACT

A new and distinct rose plant having a strong fragrance and pale purple-colored flowers.

4 Drawing Sheets

Botanical classification: *Rosa* L.
Varietal denomination: 'RNF Purple 01'.

BACKGROUND OF THE INVENTION

The present invention comprises a new and distinct cultivar of Floribunda-type rose plant known by the varietal name 'RNF Purple 01'. The new variety was discovered in April of 2010 in Gifu, Japan. The new variety is the result of a planned breeding program between an unpatented *Rosa* L. variety named 'Blue Moon' (female parent) and an unnamed and unpatented *Rosa rugosa* variety (male parent) from the breeder's own collection. 'RNF Purple 01' differs from its female parent in petal shape and the fact that the new variety has a fragrance, but 'Blue Moon' does not. Additionally, 'RNF Purple 01' exhibits a similar petal shape and existence of a fragrance to its male parent, but differs from its male parent in its actual fragrance and 'RNF Purple 01' has fewer thorns and more leaves. When 'RNF Purple 01' is compared to *Rosa* L. 'Wish AI' (currently unpatented in the U.S., Japanese Patent No. 21842), the varieties are similar in that they both exhibit a fragrance, lack eyes on the flowers, and are double-flowering in nature. The new variety differs from 'Wish AI' in petal color and shape and also exhibits a stronger fragrance than 'Wish AI'. When generally compared to other rose varieties known to the breeder, the new variety differs in its strong fragrance, its type of fragrance, and in flower color. 'RNF Purple 01' has been trial and field tested and has been found to retain its distinctive characteristics and remain true to type through successive propagations.

DESCRIPTION OF THE DRAWINGS

The accompanying photographic drawings illustrate the new variety taken from 3-4 years of age, with the color being as nearly true as is possible with color illustrations of this type.

DESCRIPTION OF THE PLANT

Figure 1:
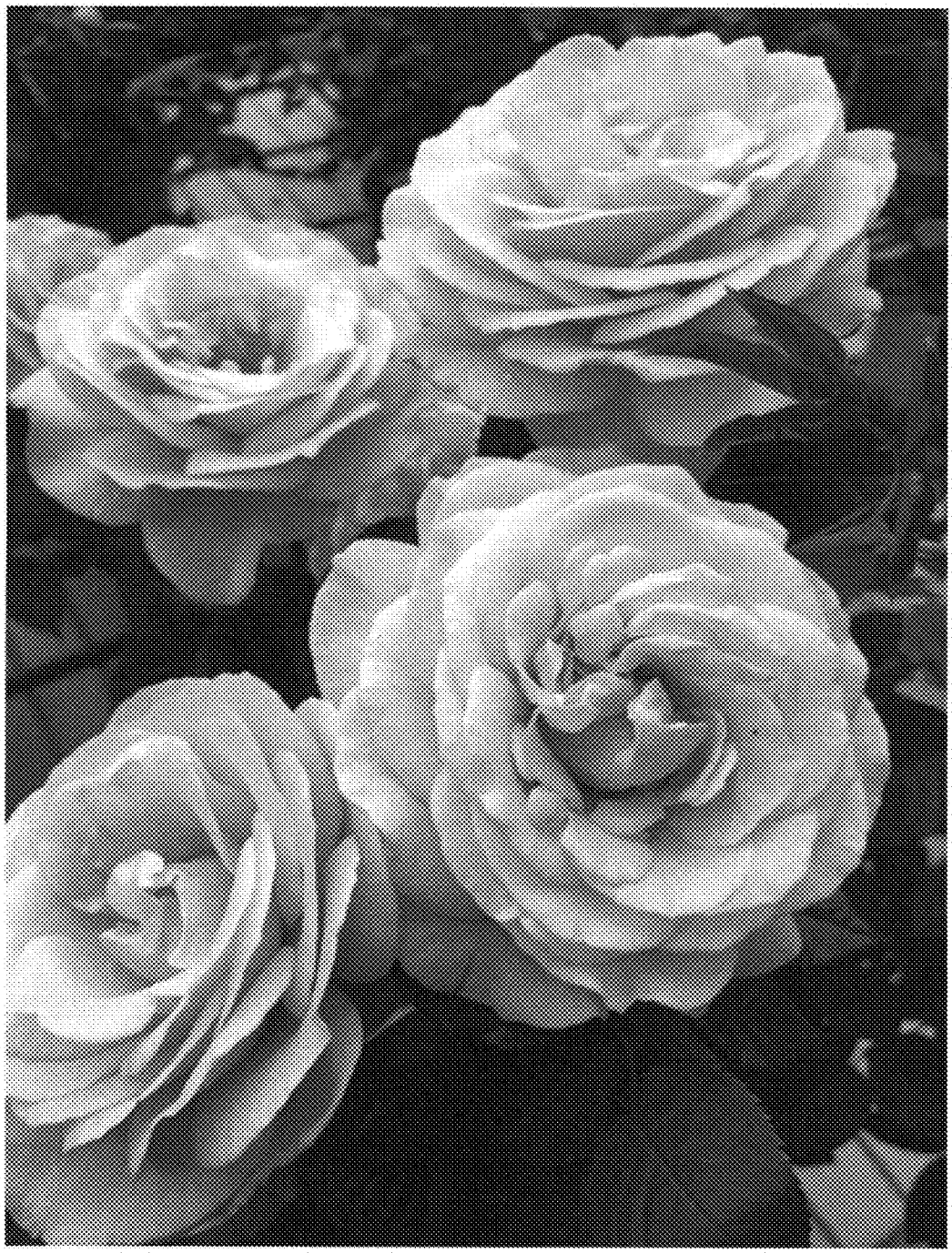
FIG. 1 shows a close-up view of the blooms of the new variety.
Figure 2:
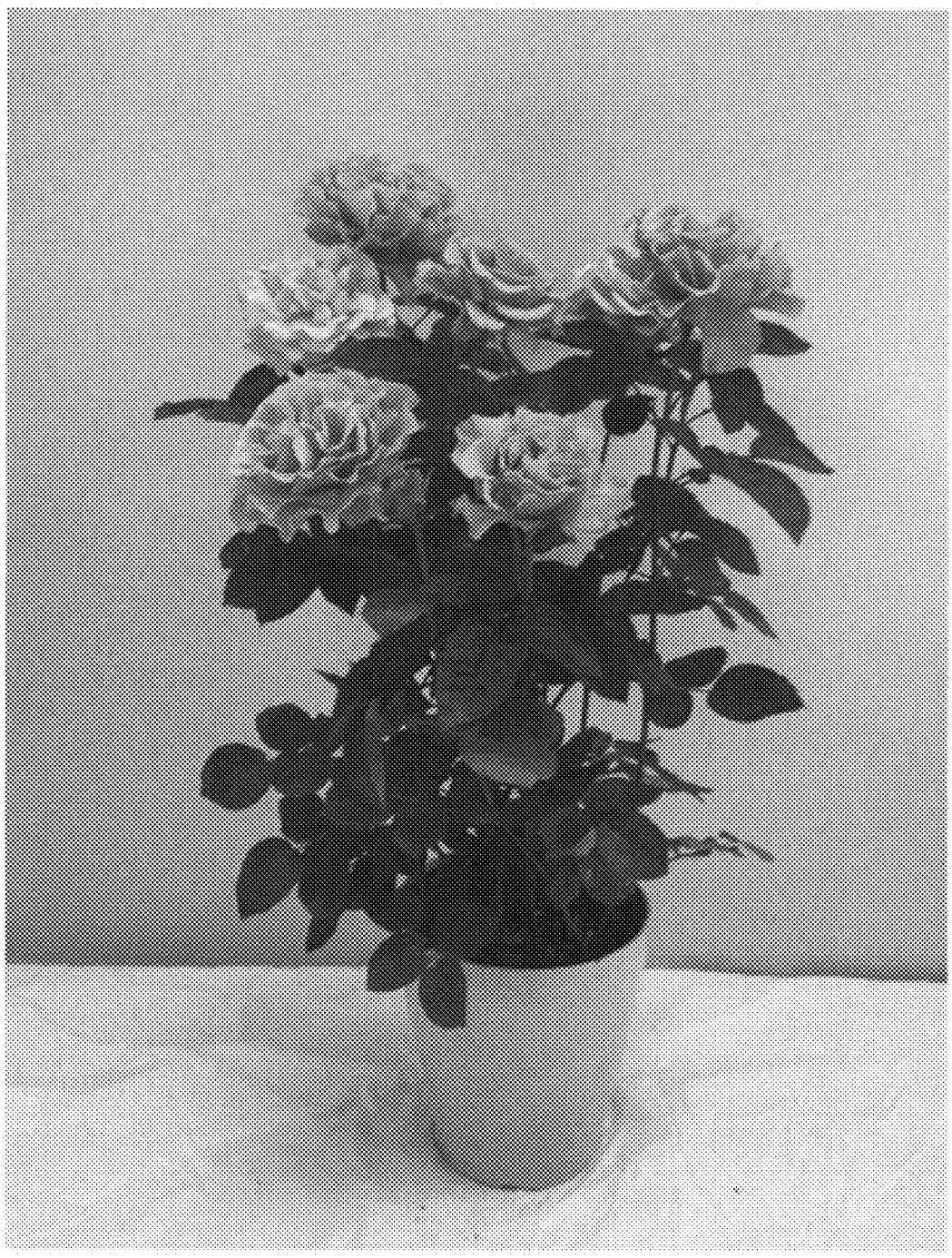
FIG. 2 shows a view of the new variety grown to a flowering plant.
Figure 3:
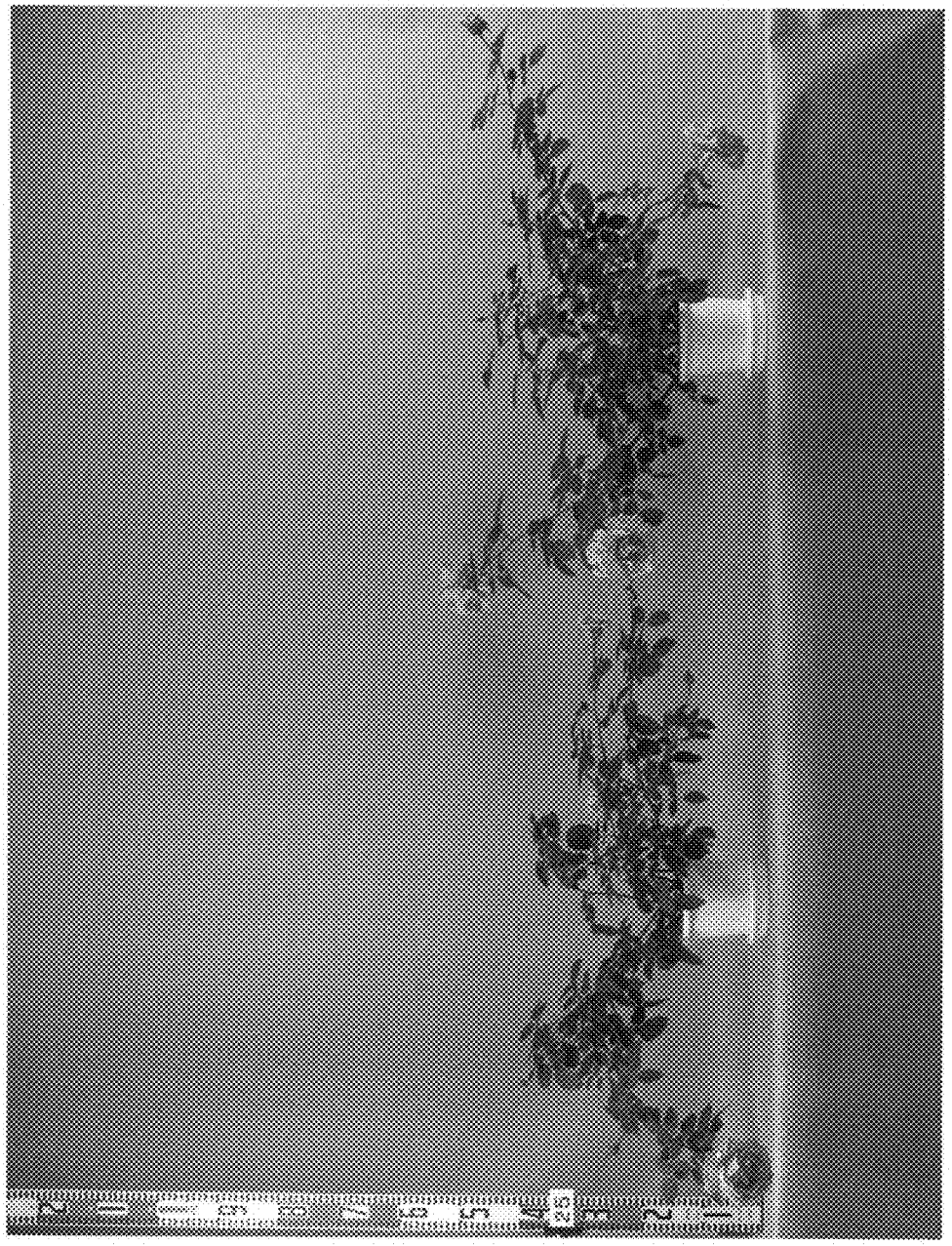
FIG. 3 shows a view of multiple plants of the new variety.
Figure 4:
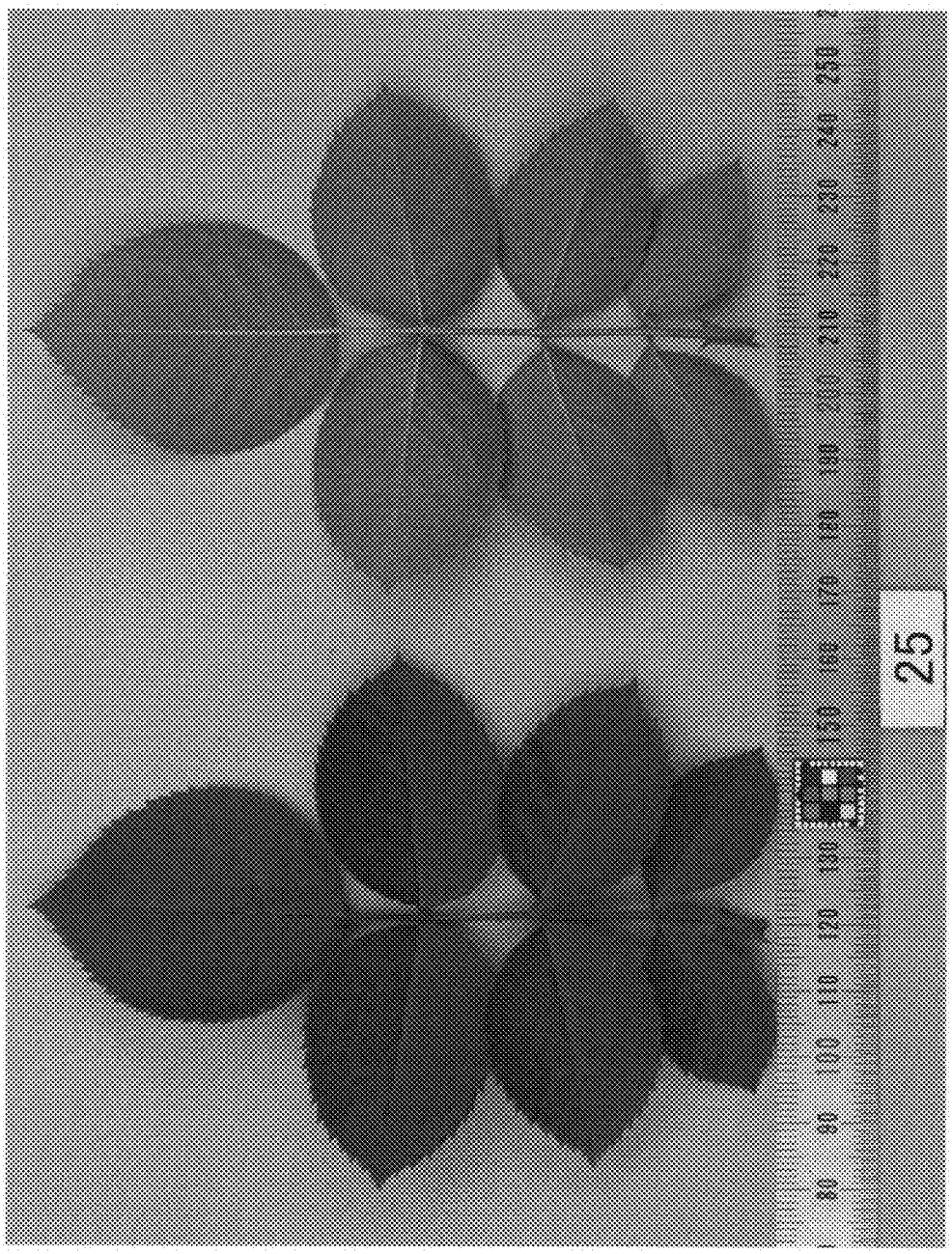
FIG. 4 shows the leaves of the new variety.

The following detailed description sets forth the characteristics of the new cultivar. The data which defines these characteristics were collected by asexual reproductions first performed via stem cuttings in May of 2011 carried out in Gifu, Japan. Plants of the new variety were grown in a greenhouse under natural light in 15 cm pots with peat moss substrate and with the assistance of heaters in the winter. The color readings and measurements were taken indoors in a greenhouse under natural light on one-year-old plants grown in containers. Color references are primarily to The 2015 R.H.S. Colour Chart of The Royal Horticultural Society of London, Sixth Edition.

PLANT

Time to initiate roots: About 21-28 days at approximately 25° C.

Time to develop roots: About 30-45 days at approximately 25° C.

Time to produce a finished flowering plant from a rooted cutting: About 5 months/20-22 weeks in a 15 cm container.

Rooting habit: Similar to standard roses.

Form: Upright.

Distance from media surface to top of foliage: 30-35 cm at the end of production.

Distance from media surface to top of flowers: 35-40 cm.

Plant diameter: Around 25 cm.

Vigor: Average.

Strength (need for artificial support): No artificial support needed.
Branching characteristics: Branching from bottom or lower level.
Stem color:
*Immature*.—N57A.
*Mature*.—135C.
Surface texture:
*Young wood*.—Smooth and hard.
*Older wood*.—Rough and scabrous.
Average stem diameter: From 7 mm to 1 cm.
Internode length: Approximately 4 to 5 cm.
Number of internodes: 6 to 7.
Thorns:
*Average number*.—Main branches: 70 per plant. Stems: 10 per stem.
*Length*.—7 mm to 1 cm.
*Width*.—Around 5 mm.
*Color*.—Immature: 60B and 63C. Mature: 166C.
*Shape*.—Acuminate.
Foliage:
*Arrangement*.—Alternate.
*Average number of leaves per lateral branch*.—7.
*Average number of leaflets per leaf*.—7.
*Overall size of leaf*.—Length: 10 cm. Width: 5 cm.
*Leaflet*.—Shape of leaf (generally): Ovate. Shape of apex: Acute. Shape of base: Obtuse. Length range: 5-7 cm. Width range: 3-5 cm. Texture: Moist and smooth. Margin type: Serrate and similar to standard roses. Color: Young leaves: Upper surface: 146B. Lower surface: 68C. Mature leaves: Upper surface: 137A. Lower surface: 132D. Veins: Venation type: Pinnate. Color: 127A.
*Petiole*.—Length: 2-3 mm. Diameter: 1-2 mm. Color: 137D with a hint of 60A. Texture: Smooth.
*Stipule*.—None present.

INFLORESCENCE

Buds:
*Number of buds per plant*.—10.
*Number of buds per flowering stem*.—2.
*Shape of individual bud*.—Napiform.
*Length of individual bud*.—1.5-2 cm.
*Width of individual bud*.—8 mm to 1 cm.
*Bud color*.—Green (144D) with red (58B).
Natural flowering season at specified location: End of April to May in Gifu, Japan.
Average number of flowers per year at specified location: 10 to 15.
Flowering habit: Continuous and freely flowering.
Flower description: 2 or more flowers and bloom like a bunch.
Lastingness of an individual flower on the plant: 10 days to 2 weeks.
Lastingness of a cut flower: 1 week.
Flower:
*General appearance*.—Double flowering rose.
*Shape*.—Round and mounded.
*Diameter*.—8-10 cm.
*Height*.—3-4 cm.
Petals:
*Color*.—Upper and lower surfaces (when opening): 84C. Upper and lower surfaces (fully opened): 84C.
*Shape*.—Rounded.
*Length*.—4-5 cm.
*Width*.—5-6 cm.
*Apex shape*.—Round with a wide lip.
*Base shape*.—Round and narrow.
*Margin*.—Entire.
*Number per flower*.—25-35.
*Texture*.—Soft.
*Reflex characteristics*.—None.
*Presence of basal petal spots*.—None.
*Petaloid description*.—Lightly fringed with semi-double flowering.
Sepals:
*Upper surface color*.—When opening: 149D. Fully opened: 193A.
*Lower surface color*.—When opening: 145C. Fully opened: 193D.
*Shape*.—Sharp.
*Length*.—2-3 cm.
*Width*.—8 mm to 1 cm.
*Apex shape*.—Pointed.
*Base shape*.—Wide.
*Margin*.—Entire and tight, when closed.
*Number per flower*.—4-5.
*Texture*.—Soft and smooth.
Pedicel:
*Length*.—3-5 cm.
*Diameter*.—3 mm.
*Texture*.—Tough, with small thorns present.
*Strength*.—Strong.
*Color*.—142C.
Peduncle:
*Length*.—6.4 cm.
*Diameter*.—4.8 mm.
*Color*.—142C.
Receptacle:
*Texture*.—Sleek.
*Shape*.—Semicircle.
*Height*.—5-7 mm.
*Width*.—5-7 mm.
*Color*.—143B.
Fragrance: Strong.
Disease/pest resistance: Average resistance to powdery mildew of the *Erysiphaceae* family.
Winter temperature tolerance: Blooming at 1° C. in winter. With only roots, −15~-18° C.
Hot temperature tolerance: 40° C.
Drought tolerance: Average.
Reproductive organs:
Stamens:
*Number (per flower)*.—50.
*Filament*.—Length: 7-10 mm. Color: NN155C.
*Anthers*.—Shape: Like a match stick. Length: 2-3 mm. Color: 164D.
*Pollen*.—Color: 12A. Amount (generally): Less than average.
Pistils:
*Number*.—50.
*Length*.—1-2 mm.
*Style*.—Length: 7.8 mm. Color: 157D.
*Stigma*.—Shape: Funnel. Color: 165D. Size: 1 mm.
*Ovaries*.—Length: 3 mm. Width: 0.5 mm. Color: 157D.

I claim:

1. A new and distinct variety of rose plant, as is herein illustrated and described.

* * * * *